(12) United States Patent
Gordon

(10) Patent No.: US 9,486,466 B2
(45) Date of Patent: Nov. 8, 2016

(54) VELIPARIB IN COMBINATION WITH CARBOPLATIN FOR THE TREATMENT OF TRIPLE NEGATIVE BREAST CANCER

(71) Applicant: AbbVie Inc., North Chicago, IL (US)

(72) Inventor: Gary Gordon, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/565,645

(22) Filed: Dec. 10, 2014

(65) Prior Publication Data

US 2015/0157652 A1 Jun. 11, 2015

Related U.S. Application Data

(60) Provisional application No. 61/914,216, filed on Dec. 10, 2013.

(51) Int. Cl.

| | |
|---|---|
| *A61K 31/704* | (2006.01) |
| *A61K 31/4184* | (2006.01) |
| *A61K 31/337* | (2006.01) |
| *A61K 31/282* | (2006.01) |
| *A61K 31/664* | (2006.01) |
| *A61K 31/41* | (2006.01) |
| *A61K 31/4164* | (2006.01) |

(52) U.S. Cl.
CPC .......... *A61K 31/704* (2013.01); *A61K 31/282* (2013.01); *A61K 31/337* (2013.01); *A61K 31/41* (2013.01); *A61K 31/4164* (2013.01); *A61K 31/4184* (2013.01); *A61K 31/664* (2013.01)

(58) Field of Classification Search
CPC .......... A61K 31/704; A61K 31/4184; A61K 31/337; A61K 31/282; A61K 31/664
USPC .................................. 514/34, 394
See application file for complete search history.

(56) References Cited

U.S. PATENT DOCUMENTS

| | | | | |
|---|---|---|---|---|
| 2013/0012465 A1* | 1/2013 | Haslinger | ............ | A61K 31/337 514/34 |
| 2013/0224312 A1* | 8/2013 | Kaufmann | ........... | C12Q 1/6876 424/649 |

FOREIGN PATENT DOCUMENTS

| | | |
|---|---|---|
| WO | WO-2006110816 A2 | 10/2006 |
| WO | WO-2007084532 A2 | 7/2007 |

OTHER PUBLICATIONS

Bandyopadhyay et al. Physical Interaction between Epidermal Growth Factor Receptor and DNA-dependent Protein Kinase in Mammalian Cells. J Biol Chem vol. 273, No. 3, pp. 1568-1573, 1998.*

Abdulkarim et al. Increased Risk of Locoregional Recurrence for Women With T1-2N0 Triple-Negative Breast Cancer Treated With Modified Radical Mastectomy Without Adjuvant Radiation Therapy Compared With Breast-Conserving Therapy. J Clin Oncol 29:2852-2858, 2011.*

Chen X.S., et al., "Weekly Paclitaxel Plus Carboplatin is an Effective Nonanthracycline-Containing Regimen as Neoadjuvant Chemotherapy for Breast Cancer," Annals of Oncology, 2010, vol. 21 (5), pp. 961-967.

Chia J.W., et al., "Triple-Negative Metastatic/Recurrent Breast Cancer: Treatment with Paclitaxel/Carboplatin Combination Chemotherapy," Journal of Clinical Oncology, 2007, vol. 25 (18S), p. 1086.

Donawho C.K., et al., "ABT-888, an Orally Active Poly(ADP-Ribose) Polymerase Inhibitor that Potentiates DNA-Damaging Agents in Preclinical Tumor Models," Clinical Cancer Research, 2007, vol. 13 (9), pp. 2728-2737.

International Search Report and Written Opinion for Application No. PCT/US2014/069501, mailed on Mar. 26, 2015, 09 pages.

Isakoff S.J., et al., "Abstract OT2-3-07: A Randomized, Phase 2 Study of the Poly (ADP-ribose) Polymerase (PARP) Inhibitor Veliparib (ABT-888) in Combination with Temozolomide (TMZ) or in Combination with Carboplatin (C) and Paclitaxel (P) Versus Placebo plus C/P in subjects with BRCA1 or BRACA2 Mutation and Metastatic Breast Cancer," Cancer Research, 2012, vol. 72 (24 Suppl).

Kummar S., et al., "Phase 0 Clinical Trial of the Poly(ADP-Ribose)Polymerase Inhibitor ABT-888 in Patients with Advanced Malignancies," Journal of Clincal Oncology, 2009, vol. 27 (16), pp. 2705-2711.

Santana-Davila, R., et al., "Treatment Options for Patients with Triple-Negative Breast Cancer," Journal of Hematology and Oncology, 2010, vol. 3 (42), 11 pages.

Virag L., et al., "The Therapeutic Potential of Poly(ADP-ribose) Polymerase Inhibitors," Pharmacological Reviews, 2002, vol. 54 (3), pp. 375-429.

Nowsheen, Somaira et al. "Cetuxmab Augments Cytoxcity with Poly (ADP-Ribose) Polymerase Inhibition in Head and Neck Cancer" PLoS One, vol. 6, issue 8, Aug. 2011, pp. 1-11.

O'Shaghnesssy, J. et al. "Oral Abstract Session, Breast Cancer—Triple-Negative/Cytoxics/Local Therapy." ASC University Meeting Library (http://meetinglibrary.asco.org)/content/78038-102), downloaded Jan. 29, 2016, 2 pages.

Oonk, A. M. M. et al. "Clinical Correlates of 'BRCAness' in Triple-Negative Breast Cancer Patients Receiving Adjuvant Chemotherapy" Annals of Onocolgy. Published Feb. 21, 2012, 5 pages.

* cited by examiner

*Primary Examiner* — Clinton Brooks
*Assistant Examiner* — Yih-Horng Shiao
(74) *Attorney, Agent, or Firm* — Quarles & Brady LLP

(57) ABSTRACT

The invention relates to a method for the treatment of triple negative breast cancer in a subject, comprising administering to the subject an effective amount of 2-[(2R)-2-methylpyrrolidin-2-yl]-1H-benzimidazole-4-carboxamide, or a pharmaceutically acceptable salt thereof, and an effective amount of carboplatin, in combination with standard of care.

14 Claims, No Drawings

VELIPARIB IN COMBINATION WITH CARBOPLATIN FOR THE TREATMENT OF TRIPLE NEGATIVE BREAST CANCER

This application claims the benefit of U.S. Provisional Patent Application No. 61/914,216, filed on Dec. 10, 2013, the entirety of which is hereby incorporated by reference.

FIELD OF THE INVENTION

This invention pertains to the use of veliparib and carboplatin in the treatment of subjects with triple negative breast cancer.

BACKGROUND OF THE INVENTION

Invasive breast carcinoma is a group of malignant epithelial tumors characterized by invasion of adjacent tissues and a marked tendency to metastasize to distant sites. Breast cancer exhibits a wide range of morphological phenotypes and specific histopathological types that have particular prognostic and clinical characteristics. For example, subtypes are stratified according to their estrogen receptor (ER), progesterone receptor (PR) and human epidural growth factor receptor (HER2) status. For many patients, targeted therapies against one of the receptor targets are available. However, 10-20% of mammary tumors lack hormone receptors (ER/PR) and do not overexpress Her2/neu protein, clinically defined as triple negative breast cancer.

Triple negative breast cancers are more aggressive than ER/PR+ tumors or Her2+ tumors, and there are no targeted therapies available for this disease. The use of an anthracycline, taxane, and an alkylating agent is recommended. However, a large number of patients treated with chemotherapy and surgery for early breast cancer (EBC) are not cured of their disease. Approximately 30% to 40% of patients with TNBC will have a recurrence of disease within 3 to 10 years of treatment with neoadjuvant therapy and surgery. Most patients with recurrent disease will die from their breast cancer. Therefore, identification of therapeutic advances is critical.

Poly (ADP-ribose) polymerase (PARP) is a nuclear enzyme that recognizes DNA damage and facilitates DNA repair. PARP activity is required for the repair of single-stranded DNA breaks through the base excision repair pathways. Cancer cells are often deficient in double-stranded DNA-repair capability, and are therefore more dependent on PARP directed single-stranded DNA-repair than are normal cells. Consequently, inhibition of PARP enhances the anti-tumor effects of DNA-damaging agents in many cancer cells.

Most early breast cancers are treated with multi-modality therapy (surgery+/−radiotherapy+chemotherapy). Multiple large randomized trials have demonstrated identical outcomes may be obtained irrespective of the order of surgery and chemotherapy. Thus neoadjuvant (chemotherapy followed by surgery) and adjuvant (surgery followed by chemotherapy) treatment regimens are considered equivalent. One advantage of neoadjuvant therapy is that tumor responses to chemotherapy can be measured, unlike in the adjuvant setting where all known tumor is surgically removed prior to chemotherapy. The tumor response to neoadjuvant chemotherapy provides significant prognostic information. Those patients that achieve complete pathological tumor responses (no living cancer cells can be identified in the surgical specimen) have significantly better prognoses than those that do not.

It has been discovered that the PARP inhibitor veliparib, 2-[(2R)-2-methylpyrrolidin-2-yl]-1H-benzimidazole-4-carboxamide, acts synergistically in combination with the DNA-damaging agent carboplatin to increase the efficacy of the current standard-of-care treatment for early triple negative breast cancer. Adding veliparib and carboplatin to the standard of care increases the number of women that achieve pCR status in a neoadjuvant setting. This is estimated to translate into additional treated women remaining free of disease at 5 years. This is also expected increase the number of patients who would become eligible for less extensive surgery (fewer mastectomies, more breast-conserving surgery).

BRIEF SUMMARY OF THE INVENTION

The present invention relates to a method for the treatment of ER-negative, PR-negative, and HER-2 negative cancer of the breast in a subject, comprising administering to the subject 50 mg of 2-[(2R)-2-methylpyrrolidin-2-yl]-1H-benzimidazole-4-carboxamide twice a day continuously for twelve weeks; 80 mg/m$^2$ paclitaxel on day 1 of twelve 7-day cycles; and AUC 6 mg/mL/min carboplatin on day 1 of four 21-day cycles.

DETAILED DESCRIPTION OF THE INVENTION

Definitions

The terms "treat", "treating" and "treatment" refer to a method of alleviating or abrogating a disease and/or its attendant symptoms.

By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

"Effective amount" or a "pharmaceutically-effective amount" in reference to 2-[(2R)-2-methylpyrrolidin-2-yl]-1H-benzimidazole-4-carboxamide refers to the amount sufficient to induce a desired biological, pharmacological, or therapeutic outcome in a subject.

Triple negative breast cancer (TNBC) is defined by the absence of estrogen receptor (ER), progesterone receptor (PR), and HER2/neu overexpression.

Pathological Complete Response (pCR) is the absence of any residual invasive cancer on hematoxylin and eosin evaluation of the resected breast specimen and any resected lymph node tissue following completion of neoadjuvant systemic therapy.

Breast Conservation Rate (BCR) is the rate of eligibility for breast conservation after neoadjuvant therapy among subjects for whom mastectomy was planned diagnosis.

Event Free Survival (EFS) is defined as the time from random assignment to the document of the first of the following events: failure to reach potential curative surgery; local regional, or distance recurrence of breast cancer following curative surgery; a new breast cancer; another new onset malignancy, or death as a result of any cause.

Overall Survival (OS) is defined as the number of days from the day the subject is randomized to the date of the subject's death.

Clinical Response Rate (CRR) is defined as the proportion of subjects with complete or partial response as determined by imaging. For example, CR and PR can be assessed by MRI after a period of therapy (such as 12 weeks) and categorized according to percent reduction in tumor size.

Residual Cancer Burden is a numerical index of four classes to measure residual disease by combining histopathologic components of residual disease (cellularity, overall diameter, number and extent of nodal involvement). Subjects with RCB=0 are classified pCR.

Early-stage breast cancer is cancer has not spread beyond the breast or the axillary lymph nodes.

Primary Tumor Categories

T1: Tumor is 2 cm (¾ of an inch) or less across.

T2: Tumor is more than 2 cm but not more than 5 cm (2 inches) across.

T3: Tumor is more than 5 cm across.

T4: Tumor of any size growing into the chest wall or skin.

Nearby Lymph Nodes

N0: Cancer has not spread to nearby lymph nodes.

N1: Cancer has spread to 1 to 3 axillary (underarm) lymph node(s), and/or tiny amounts of cancer are found in internal mammary lymph nodes (those near the breast bone) on sentinel lymph node biopsy.

N2: Cancer has spread to 4 to 9 lymph nodes under the arm, or cancer has enlarged the internal mammary lymph nodes (but not both).

The present invention provides a method for the treatment of triple negative breast cancer in a subject, comprising administering to the subject an effective amount of veliparib, or a pharmaceutically acceptable salt thereof, in combination with an effective amount of carboplatin, in addition to standard of care.

According to current guidelines, standard of care chemotherapy should contain anthracyclines and taxanes. Multiple combinations and schedules that are recommended include concurrent or sequential anthracyclines and taxanes. Among the commonly used regimens is doxorubicin and cyclophosphamide followed by paclitaxel or the same combination given in reverse sequence.

In the present invention, the subject has ER-negative, PR-negative, and HER-2 negative (triple-negative) cancer of the breast. Triple negative tumors are defined as:

For ER- and PR-negative: less than or equal to 1% tumor staining by immunohistochemistry.

For HER-2 negative, defined as IHC 0-1+ OR HER2-neu negative according to ASCO-CAP guideline recommendations.

In another embodiment, the subject has a diagnosis of a BRCA1 and/or a BRCA2 mutation. The mutation may be a deleterious mutation. The mutation may be a germline mutation or a somatic mutation.

In one embodiment, the subject has early-stage breast cancer. In one embodiment, the subject has clinical stage T2-4 N0-2 or T1 N1-2 invasive breast cancer. The subject may have multiple lesions, e.g., up to 2. In another embodiment, the subject is a candidate for potentially curative surgery.

In one embodiment, the subject has definitive breast surgery, either mastectomy or breast conserving surgery. The chemotherapy of the invention may be adjuvant therapy (surgery followed by chemotherapy) or neoadjuvant therapy (chemotherapy followed by surgery). In the case of neoadjuvant therapy, breast surgery is performed approximately 4 to 8 weeks after the subject's last dose.

2-[(2R)-2-methylpyrrolidin-2-yl]-1H-benzimidazole-4-carboxamide is an inhibitor of poly(ADP-ribose)polymerase (PARP) and has been previously described in WO 2006-110816. Poly(ADP-ribose)polymerase has an essential role in facilitating DNA repair, controlling RNA transcription, mediating cell death, and regulating immune response. These actions make PARP inhibitors targets for a broad spectrum of disorders. (Virag L., et al., Pharmacol. Rev. 2002 54(3):375-429). In various preclinical cancer models and human clinical trials, PARP inhibitors have been shown to potentiate radiation and chemotherapy by increasing apoptosis of cancer cells, limiting tumor growth, decreasing metastasis, and prolonging the survival of tumor-bearing subjects. (WO 2007-084532; Donawho C. K., et al., Clin Cancer Res 2007 13(9):2728-37; Kummar S., et al., J Clin Oncol. 2009 27(16):2705-11).

This invention also is directed, in part, to all salts of 2-[(2R)-2-methylpyrrolidin-2-yl]-1H-benzimidazole-4-carboxamide and methods of their use. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of 2-[(2R)-2-methylpyrrolidin-2-yl]-1H-benzimidazole-4-carboxamide can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of 2-[(2R)-2-methylpyrrolidin-2-yl]-1H-benzimidazole-4-carboxamide include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

This invention also is directed, in part, to all compositions of 2-[(2R)-2-methylpyrrolidin-2-yl]-1H-benzimidazole-4-carboxamide and methods of their use. 2-[(2R)-2-methylpyrrolidin-2-yl]-1H-benzimidazole-4-carboxamide may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising 2-[(2R)-2-methylpyrrolidin-2-yl]-1H-benzimidazole-4-carboxamide to be administered orally include, but are not limited to, agar, alginic acid, aluminum hydroxide, benzyl alcohol, benzyl benzoate, 1,3-butylene glycol, carbomers, castor oil, cellulose, cellulose acetate, colloidal silica, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, microcrystalline cellulose, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, titanium dioxide, tragacanth, tetrahydrofurfuryl alcohol, triglycerides, water, mixtures thereof and the like.

In one embodiment of the invention, the dose of veliparib, or a pharmaceutically acceptable salt or solvate thereof, is 50 mg twice a day continuously for twelve weeks (first segment).

Also during the first segment, carboplatin is administered intravenously at a dose of AUC 6 mg/mL/min on Day 1 of four 21-day cycles.

Also during the first segment, paclitaxel is administered intravenously at a dose of 80 mg/m$^2$ on Day 1 of twelve weekly cycles.

In another embodiment of the invention, the first segment is followed by a second chemotherapy segment. In the second segment, 60 mg/m$^2$ of doxorubicin will be administered intravenously on Day 1 of four 14 day cycles, and 600 mg/m$^2$ of cyclophosphamide will be administered intravenously on Day 1 of four 14 days cycles.

Alternatively, 60 mg/m$^2$ of doxorubicin will be administered intravenously on Day 1 of four 21 day cycles, and 600 mg/m$^2$ of cyclophosphamide will be administered intravenously on Day 1 of four 21 days cycles.

The dose of veliparib may be delayed at any time during the first segment due to toxicity and resumed at the starting dose.

Likewise, the dose of carboplatin and/or the dose of paclitaxel may be independently delayed at any times during the first segment due to toxicity and resumed at the starting dose. If both carboplatin and paclitaxel are delayed, then 2-[(2R)-2-methylpyrrolidin-2-yl]-1H-benzimidazole-4-carboxamide is also delayed. In the case of delays, the period of the first segment may be twelve weeks, thirteen weeks, fourteen weeks, fifteen weeks, or sixteen weeks. The period of the first segment may not exceed sixteen weeks. If the first segment extends through sixteen weeks, the first segment is discontinued and the second segment commences.

Alternatively, the dose of veliparib, paclitaxel, carboplatin, doxorubicin, and/or cyclophosphamide may be reduced. Reductions in dose level are show in Table 1. Once dose levels are decreased, they are not re-escalated.

TABLE 1

| Dose level | Carboplatin | Paclitaxel | Doxorubicin | Cyclophosphamide | Veliparib |
|---|---|---|---|---|---|
| Starting Dose Level | AUC 6 | 80 mg/m$^2$ | 60 mg/m$^2$ | 600 mg/m$^2$ | 50 mg |
| Dose Level -1 | AUC 5 | 70 mg/m$^2$ | 50 mg/m$^2$ | 500 mg/m$^2$ | 40 mg |
| Dose Level -2 | AUC 4 | 60 mg/m$^2$ | 40 mg/m$^2$ | 400 mg/m$^2$ | N/A |

Other PARP inhibitors are known in the art, including olaparib, BMN 673, rucaparib, iniparib, INO-1001, E7016, CEP-9722, AZD2461, MK-4827, and JP-289.

These other PARP inhibitors can also be combined with platins in a first segment in addition to the standard of care.

Suitable doses for a PARP inhibitor in the first segment are 5 mg/day to 250 mg/day. Alternatively, suitable doses for a PARP inhibitor in the first segment are 10 mg/day to 150 mg/day. Alternatively, suitable doses for a PARP inhibitor in the first segment are 25 mg/day to 100 mg/day. Suitable doses include 5 mg/day, 10 mg/day, 15 mg/day, 20 mg/day, 25 mg/day, 30 mg/day, 35 mg/day, 40 mg/day, 50 mg/day, 55 mg/day, 60 mg/day, 65 mg/day, 70 mg/day, 75 mg/day, 80 mg/day, 85 mg/day, 90 mg/day, 95 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, or 250 mg/day.

In the case of neoadjuvant therapy of a first segment and a second segment of the invention, the subject may have a pathological complete response (pCR). pCR is defined as the absence of any residual invasive cancer on hexatoxylin and eosin evaluation of the resected breast specimen and any resected lymph node tissue following completion of neoadjuvant therapy.

Also in the case of neoadjuvant therapy of a first segment and a second segment of the invention, the subject may be eligible for breast conservation even though a mastectomy was planned at diagnosis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLE

Example 1

This example is a Phase 2, interventional, randomized, open label study evaluating the safety and efficacy of veliparib and carboplatin administered concurrently with standard chemotherapy in subjects with early-stage triple negative breast cancer.

Inclusion Criteria

Female

Patients with histologically confirmed invasive cancer of the breast.

Clinically or radiologically measurable disease in the breast after diagnostic biopsy, defined as longest diameter greater than or equal to 25 mm (2.5 cm).

No prior cytotoxic regimens are allowed for this malignancy. Patients may not have had prior chemotherapy or prior radiation therapy to the ipsilateral breast for this malignancy. Prior bis-phosphonate therapy is allowed.

Age≥18 years.

ECOG performance status 0-1.

Willing to undergo core biopsy of the primary breast lesion to assess baseline biomarkers.

Non-pregnant and non-lactating.

No ferromagnetic prostheses. Patients who have metallic surgical implants that are not compatible with an MRI machine are not eligible.

Ability to understand and willingness to sign a written informed consent.

Eligible tumors must meet one of the following criteria: Stage II or III, or T4, any N, M0, including clinical or pathologic inflammatory cancer or Regional Stage IV, where supraclavicular lymph nodes are the only sites metastasis.

Any tumor ER/PgR status, any HER-2/neu status as measured by local hospital pathology laboratory and meets any tumor assay profile described in protocol section 4.1.2F.

Normal organ and marrow function: Leukocytes ≥3000/µL, Absolute neutrophil count ≥1500/µL, Platelets ≥100,000/µL, Total bilirubin within normal institutional limits, unless patient has Gilbert's disease, for which bilirubin must be ≤2.0×ULN, AST(SGOT)/ALT (SGPT) ≤1.5× institutional ULN, creatinine <1.5× institutional ULN.

No uncontrolled or severe cardiac disease. Baseline ejection fraction (by nuclear imaging or echocardiography) must by ≥50%.

No clinical or imaging evidence of distant metastases by PA and Lateral CXR, Radionuclide Bone scan, and LFTs including total bilirubin, ALT, AST, and alkaline phosphatase.

Tumor assay profile must include on of the following: MammaPrint High, any ER status, any HER2 status, or MammaPrint Low, ER negative (<5%), any HER2 status, or MammaPrint Low, ER positive, HER2/neu positive by any one of the three methods used (IHC, FISH, TargetPrint™).

Exclusion Criteria

Use of any other investigational agents within 30 days of starting study treatment.

History of allergic reactions attributed to compounds of similar chemical or biologic composition to the study agent or accompanying supportive medications.

Uncontrolled intercurrent illness including, but not limited to, ongoing or active infection, symptomatic congestive heart failure, unstable angina pectoris, cardiac arrhythmia, or psychiatric illness/social situations that would limit compliance with study requirements.

Dosing

Patients received 50 mg po bid during the 12 weekly treatment cycles post-randomization and carboplatin: AUC 6 IV every three weeks for four weeks during the 12 weekly treatment cycles post-randomization with standard chemotherapy or alternatively standard chemotherapy alone. Standard chemotherapy was paclitaxel: 80 mg/m$^2$ IV during the 12 weekly treatment cycles post randomization; doxorubicin: 60 mg/m$^2$ IV after completion of the 12 weekly treatment cycles and prior to surgery for weeks 13-16; cyclophosphamide: 600 mg/m$^2$ IV after completion of the 12 weekly treatment cycles and prior to surgery for weeks 13-16.

Efficacy

Primary Outcome Measure

Determine whether adding veliparib and carboplatin to standard neoadjuvant medications increases the probability of pathologic complete response (pCR) over standard neoadjuvant chemotherapy for triple negative breast cancer.

Secondary Outcome Measures

Establishing predictive and prognostic indices based on qualification and exploratory markers to predict pCR and residual cancer burden (RCB).

To determine three- and five-year relapse-free survival (RFS) and OS among the treatment arms. [Time Frame: Three- and Five-Year Post-surgery Follow-up].

To determine incidence of adverse events (AEs), serious adverse events (SAEs), and laboratory abnormalities of each investigational agent tested. [Time Frame: Post-Randomization, Pre-AC, Pre-Surgery, Post-Surgery up to One Year during follow-up].

22 subjects received standard chemotherapy followed by surgery (control) while 39 patients received veliparib and carboplatin in addition to standard chemotherapy followed by surgery.

TABLE 2

|  | pCR % |
| --- | --- |
| Control arm | 23% (n = 22) |
| Veliparib arm | 56% (n = 39) |

What is claimed is:

1. A method for the treatment of ER-negative, PR-negative, and HER-2 negative cancer of the breast in a subject, comprising administering to the subject in need thereof a first chemotherapy segment comprising administering
    (a) 50 mg of 2-[(2R)-2-methylpyrrolidin-2-yl]-1H-benzimidazole-4-carboxamide twice a day continuously for twelve weeks;
    (b) 80 mg/m$^2$ paclitaxel on day 1 of twelve 7-day cycles; and
    (c) area under the curve (AUC) 6 mg/mL/min carboplatin on day 1 of four 21-day cycles.

2. The method of claim 1, wherein the first chemotherapy segment is followed by a second chemotherapy segment comprising administering to the subject
    (a) 60 mg/m$^2$ doxorubicin on day 1 of four 14-day cycles; and
    (b) 600 mg/m$^2$ cyclophosphamide on day 1 of four 14-day cycles.

3. The method of claim 1, wherein the first chemotherapy segment is followed by a second chemotherapy segment comprising administering to the subject
    (a) 60 mg/m$^2$ doxorubicin on day 1 of four 21-day cycles; and
    (b) 600 mg/m$^2$ cyclophosphamide on day 1 of four 21-day cycles.

4. The method of claim 1, wherein the subject has early-stage breast cancer.

5. The method of claim 1, wherein the subject is a candidate for surgery.

6. The method of claim 5, wherein the subject has surgery approximately 4-8 weeks after the last chemotherapy treatment.

7. The method of claim 6, wherein the subject has a mastectomy.

8. The method of claim 6, wherein the subject has breast conservation surgery.

9. The method of claim 1, wherein the ER-negative, PR-negative, and HER-2 negative cancer of the breast has a BRCA1 mutation.

10. The method of claim 1, wherein the ER-negative, PR-negative, and HER-2 negative cancer of the breast has a BRCA2 mutation.

11. The method of claim 1, wherein step (a) 50 mg of 2-[(2R)-2-methylpyrrolidin-2-yl]-1H-benzimidazole-4-carboxamide is administered twice a day continuously for twelve weeks.

12. The method of claim 1, wherein step (a) 70 mg of 2-[(2R)-2-methylpyrrolidin-2-yl]-1H-benzimidazole-4-carboxamide is administered twice a day continuously for twelve weeks.

13. The method of claim 1, wherein step (a) 100 mg of 2-[(2R)-2-methylpyrrolidin-2-yl]-1H-benzimidazole-4-carboxamide is administered twice a day continuously for twelve weeks.

14. The method of claim 1, wherein step (a) 120 mg of 2-[(2R)-2-methylpyrrolidin-2-yl]-1H-benzimidazole-4-carboxamide is administered twice a day continuously for twelve weeks.

* * * * *

UNITED STATES PATENT AND TRADEMARK OFFICE
CERTIFICATE OF CORRECTION

PATENT NO. : 9,486,466 B2  
APPLICATION NO. : 14/565645  
DATED : November 8, 2016  
INVENTOR(S) : Gary Gordon Page 1 of 3

It is certified that error appears in the above-identified patent and that said Letters Patent is hereby corrected as shown below:

On the Title Page

Replace Title Page with attached Title Page.

In the Specification

Column 3, Line 11, detailed description: "Early-stage breast cancer is cancer has not spread beyond" to read as --Early-stage breast cancer is cancer that has not spread beyond--

Column 4, Line 63, detailed description: "Ha" to read as --IIa--

Column 8, Line 9, Example: "by" to read as --be--

Column 8, Line 15, Example: "on" to read as --any--

In the Claims

Column 10, Lines 12-32, Claims 9-14:
Delete:
"9. The method of claim 1, wherein the ER-negative, PR-negative, and HER-2 negative cancer of the breast has a BRCA1 mutation.

10. The method of claim 1, wherein the ER-negative, PR-negative, and HER-2 negative cancer of the breast has a BRCA2 mutation.

11. The method of claim 1, wherein step (a) 50mg of 2-[(2R)-2-methylpyrrolidin-2-yl]-1H-benzimidazole-4-carboxamide is administered twice a day continuously for twelve weeks.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 9,486,466 B2

12. The method of claim 1, wherein step (a) 70mg of 2-[(2R)-2-methylpyrrolidin-2-yl]-1H-benzimidazole-4-carboxamide is administered twice a day continuously for twelve weeks.

13. The method of claim 1, wherein step (a) 100mg of 2-[(2R)-2-methylpyrrolidin-2-yl]-1H-benzimidazole-4-carboxamide is administered twice a day continuously for twelve weeks.

14. The method of claim 1, wherein step (a) 120mg of 2-[(2R)-2-methylpyrrolidin-2-yl]-1H-benzimidazole-4-carboxamide is administered twice a day continuously for twelve weeks."

(12) United States Patent
Gordon

(10) Patent No.: US 9,486,466 B2
(45) Date of Patent: Nov. 8, 2016

(54) VELIPARIB IN COMBINATION WITH CARBOPLATIN FOR THE TREATMENT OF TRIPLE NEGATIVE BREAST CANCER

(71) Applicant: AbbVie Inc., North Chicago, IL (US)

(72) Inventor: Gary Gordon, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/565,645

(22) Filed: Dec. 10, 2014

(65) Prior Publication Data

US 2015/0157652 A1 Jun. 11, 2015

Related U.S. Application Data

(60) Provisional application No. 61/914,216, filed on Dec. 10, 2013.

(51) Int. Cl.

| *A61K 31/704* | (2006.01) |
|---|---|
| *A61K 31/4184* | (2006.01) |
| *A61K 31/337* | (2006.01) |
| *A61K 31/282* | (2006.01) |
| *A61K 31/664* | (2006.01) |
| *A61K 31/41* | (2006.01) |
| *A61K 31/4164* | (2006.01) |

(52) U.S. Cl.
CPC ........... *A61K 31/704* (2013.01); *A61K 31/282* (2013.01); *A61K 31/337* (2013.01); *A61K 31/41* (2013.01); *A61K 31/4164* (2013.01); *A61K 31/4184* (2013.01); *A61K 31/664* (2013.01)

(58) Field of Classification Search
CPC .......... A61K 31/704; A61K 31/4184; A61K 31/337; A61K 31/282; A61K 31/664
USPC ..................................... 514/34, 394
See application file for complete search history.

(56) References Cited

U.S. PATENT DOCUMENTS

| 2013/0012465 A1* | 1/2013 | Haslinger | A61K 31/337 |
| | | | 514/34 |
| 2013/0224312 A1* | 8/2013 | Kaufmann | C12Q 1/6876 |
| | | | 424/649 |

FOREIGN PATENT DOCUMENTS

| WO | WO-2006110816 A2 | 10/2006 |
| WO | WO-2007084532 A2 | 7/2007 |

OTHER PUBLICATIONS

Bandyopadhyay et al. Physical Interaction between Epidermal Growth Factor Receptor and DNA-dependent Protein Kinase in Mammalian Cells. J Biol Chem vol. 273, No. 3, pp. 1568-1573, 1998.*
Abdulkarim et al. Increased Risk of Locoregional Recurrence for Women With T1-2N0 Triple-Negative Breast Cancer Treated With Modified Radical Mastectomy Without Adjuvant Radiation Therapy Compared With Breast-Conserving Therapy. J Clin Oncol 29:2852-2858, 2011.*
Chen X.S., et al., "Weekly Paclitaxel Plus Carboplatin is an Effective Nonanthracycline-Containing Regimen as Neoadjuvant Chemotherapy for Breast Cancer," Annals of Oncology, 2010, vol. 21 (5), pp. 961-967.
Chia J.W., et al., "Triple-Negative Metastatic/Recurrent Breast Cancer: Treatment with Paclitaxel/Carboplatin Combination Chemotherapy," Journal of Clinical Oncology, 2007, vol. 25 (18S), p. 1086.
Donawho C.K., et al., "ABT-888, an Orally Active Poly(ADP-Ribose) Polymerase Inhibitor that Potentiates DNA-Damaging Agents in Preclinical Tumor Models," Clinical Cancer Research, 2007, vol. 13 (9), pp. 2728-2737.
International Search Report and Written Opinion for Application No. PCT/US2014/069501, mailed on Mar. 26, 2015, 09 pages.
Isakoff S.J., et al., "Abstract OT2-3-07: A Randomized, Phase 2 Study of the Poly (ADP-ribose) Polymerase (PARP) Inhibitor Veliparib (ABT-888) in Combination with Temozolomide (TMZ) or in Combination with Carboplatin (C) and Paclitaxel (P) Versus Placebo plus C/P in subjects with BRCA1 or BRACA2 Mutation and Metastatic Breast Cancer," Cancer Research, 2012, vol. 72 (24 Suppl).
Kummar S., et al., "Phase 0 Clinical Trial of the Poly(ADP-Ribose)Polymerase Inhibitor ABT-888 in Patients with Advanced Malignancies," Journal of Clincal Oncology, 2009, vol. 27 (16), pp. 2705-2711.
Santana-Davila, R., et al., "Treatment Options for Patients with Triple-Negative Breast Cancer." Journal of Hematology and Oncology, 2010, vol. 3 (42), 11 pages.
Virag L., et al., "The Therapeutic Potential of Poly(ADP-ribose) Polymerase Inhibitors," Pharmacological Reviews, 2002, vol. 54 (3), pp. 375-429.
Nowsheen, Somaira et al. "Cetuxmab Augments Cytoxcity with Poly (ADP-Ribose) Polymerase Inhibition in Head and Neck Cancer" PLoS One, vol. 6, issue 8, Aug. 2011, pp. 1-11.
O'Shaghnesssy, J. et al. "Oral Abstract Session, Breast Cancer—Triple-Negative/Cytoxics/Local Therapy." ASC University Meeting Library (http://meetinglibrary.asco.org/content/78038-102), downloaded Jan. 29, 2016, 2 pages.
Oonk, A. M. M. et al. "Clinical Correlates of 'BRCAness' in Triple-Negative Breast Cancer Patients Receiving Adjuvant Chemotherapy" Annals of Onocolgy. Published Feb. 21, 2012, 5 pages.

* cited by examiner

*Primary Examiner* — Clinton Brooks
*Assistant Examiner* — Yih-Horng Shiao
(74) *Attorney, Agent, or Firm* — Quarles & Brady LLP

(57) ABSTRACT

The invention relates to a method for the treatment of triple negative breast cancer in a subject, comprising administering to the subject an effective amount of 2-[(2R)-2-methylpyrrolidin-2-yl]-1H-benzimidazole-4-carboxamide, or a pharmaceutically acceptable salt thereof, and an effective amount of carboplatin, in combination with standard of care.

8 Claims, No Drawings